United States Patent
Dasai et al.

(10) Patent No.: US 9,915,629 B2
(45) Date of Patent: Mar. 13, 2018

(54) METHOD FOR IDENTIFYING PH, DEVICE FOR SAME, AND METHOD FOR IDENTIFYING ION CONCENTRATION

(71) Applicant: National University Corporation Toyohashi University of Technology, Toyohashi-shi, Aichi (JP)

(72) Inventors: Fumihiro Dasai, Toyohashi (JP); Kazuaki Sawada, Toyohashi (JP); Masato Futagawa, Toyohashi (JP)

(73) Assignee: National University Corporation Toyohashi University of Technology, Aichi (JP)

( * ) Notice: Subject to any disclaimer, the term of this patent is extended or adjusted under 35 U.S.C. 154(b) by 247 days.

(21) Appl. No.: 14/758,156

(22) PCT Filed: Jan. 7, 2014

(86) PCT No.: PCT/JP2014/050073
§ 371 (c)(1),
(2) Date: Jun. 26, 2015

(87) PCT Pub. No.: WO2014/109314
PCT Pub. Date: Jul. 17, 2014

(65) Prior Publication Data
US 2015/0355127 A1 Dec. 10, 2015

(30) Foreign Application Priority Data

Jan. 11, 2013 (JP) .................................. 2013-004014

(51) Int. Cl.
*G01N 27/30* (2006.01)
*G01N 27/416* (2006.01)
*G01N 27/414* (2006.01)

(52) U.S. Cl.
CPC ....... *G01N 27/302* (2013.01); *G01N 27/4165* (2013.01); *G01N 27/4167* (2013.01); *G01N 27/4145* (2013.01)

(58) Field of Classification Search
CPC ........... G01N 27/4167; G01N 27/4165; G01N 27/302; G01N 27/4145; G01N 27/4117;
(Continued)

(56) References Cited

U.S. PATENT DOCUMENTS

| | | | |
|---|---|---|---|
| 2011/0193139 A1 | 8/2011 | Sakata et al. | |
| 2015/0101938 A1* | 4/2015 | Bychkova | G01N 27/302 205/787.5 |

FOREIGN PATENT DOCUMENTS

| | | |
|---|---|---|
| JP | 2000-55874 A | 2/2000 |
| JP | 2001-33274 A | 2/2001 |

(Continued)

OTHER PUBLICATIONS

Hattori, Toshiaki et al., Real-Time Two-Dimensional Imaging of Potassium Ion Distribution Using an Ion Semiconductor Sensor with Charged Coupled Device Technology, Analytical Sciences, 2010, vol. 26, p. 1039-1045.

(Continued)

*Primary Examiner* — Gurpreet Kaur
(74) *Attorney, Agent, or Firm* — Gavin J. Milczarek-Desai; Quarles & Brady LLP

(57) ABSTRACT

The purpose of the present invention is to measure pH of a sample with high accuracy in a pH sensor array, without the use of a glass reference electrode. Each time that a sample is measured, the potential $V_{rm}$ of the sample is identified, and the identified potential $V_{rm}$ is used to calculate the pH. The outputs $V_{oi1}$ and $V_{oi2}$ of a first element and a second element located near one another in a sensor array are represented as follows. $V_{oi1}=Si1 \times pHi1+Gi1 \times V_{rm}+Ci1$, (Continued)

Voi2=Si2×pHi2+Gi2×Vrm+Ci2. Voi is the output of the element, Si and Gi are sensitivity coefficients, and Ci is a constant, these values having been derived in advance. Here, where the potential Vrm is constant, and the elements located near one another are presumed to be at equal pH (pHi1=pHi2), the potential Vrm is identified by solving a linear equation with two unknowns.

8 Claims, 4 Drawing Sheets

(58) Field of Classification Search
CPC .. G01N 27/333; G01N 27/36; G01N 27/4035; G01N 27/3335; G01N 27/4166; G01N 27/301; G01N 27/414
See application file for complete search history.

(56) References Cited

FOREIGN PATENT DOCUMENTS

| | | |
|---|---|---|
| JP | 2009-236502 A | 10/2009 |
| JP | 2011-163826 A | 8/2011 |
| JP | 2012-207991 A | 10/2012 |

OTHER PUBLICATIONS

International Search Report for PCT/JP2014/050073, with English Translation.
Written Opinion for PCT/JP2014/050073, with English Translation.

* cited by examiner

METHOD FOR IDENTIFYING PH, DEVICE FOR SAME, AND METHOD FOR IDENTIFYING ION CONCENTRATION

TECHNICAL FIELD

The present invention relates to a method for determining pH, a device for determining pH and a method for determining ion concentration.

BACKGROUND

In the patent document 1, it is disclosed that a pH sensor array is provided with plural pH sensors arranged two-dimensionally to measure the pH distribution of a sample and output the two-dimensional image of the pH distribution measured.

In such a pH sensor array, the reference electrode is placed in contact with the sample to make the potential of the sample stable, similarly in a general pH sensor.

When the exact measurement of the pH value is required in the fields of medicine, biochemistry and so forth, a glass electrode is adopted for the reference electrode.

RELATED TECHNICAL DOCUMENT

Patent Document

Patent document 1: JP-A-2009-236502

SUMMARY OF THE INVENTION

Problems to be Solved by the Invention

A glass reference electrode is very useful for stabilizing the potential of the sample and improving the precision of pH measurement. However, the glass reference electrode is brittle since the container of the glass reference electrode is made of glass. So, if the container is broken, potassium chloride inside the container leaks out. Even if the container is not broken, potassium chloride could leak out from the connection of the container. Potassium chloride is harmful to cells. So, when the glass reference electrode is used for the sample in the fields of medicine and biochemistry, highly careful operations are required for the reference electrode. In addition, since the container of the glass reference electrode is made of glass, it is difficult to make the glass reference electrode small. From this viewpoint, the application of the pH sensor array could be limited.

On the other hand, the use of the reference electrode formed of a single body such as Pt or Ag/AgCl can prevent the reference electrode from breaking and make the reference electrode itself small easily. However, such the reference electrode generates the fluctuation of the potential of the sample to reduce the reliability of the measuring precision.

In addition, for improving the measuring precision, a method for measuring the fluctuation of the potential of the sample to correct the pH value is presented by using a REFET constituted of a sensitive film responsive not to pH but to the potential of the sample. However, due to the material limitation for the REFET, the REFET cannot be produced by a pH sensor array production line itself.

Means for Solving the Problems

The inventors of the present invention have studied intensively for solving the problems.

The inventors have come up with the exact determination of the potential of a sample by referring to the outputs of plural elements, on the presumption of "the variation" indispensably caused in the characteristic of pH sensors, namely the elements forming a sensor array, nearly equal pH values of the elements located near each other contacted with the sample, and the equipotential within the sample which is conductive in the field of medicine, biochemistry or the like.

When an element i forming a pH sensor array is contacted with a sample, the output Voi of the element i is defined as the following Equation (1).

$$Voi = Si \times pHi + Gi \times Vrm + Ci \qquad \text{Equation (1)}$$

Here, pHi is pH of the sample and Vrm is the potential of the sample when the sample is in contact with the element i. Si and Gi are sensitivity coefficients of pHi and Vrm respectively in the output Voi of the element i. Ci is a constant.

In the Equation (1), the second term of the right-hand side is attributed to the fluctuation of the potential of the sample. So, when the glass reference electrode is contacted with the sample, the potential of the sample is made stable, so that the second term could be regarded as constant. In other words, when the glass reference electrode is not used as a reference electrode, it is necessary to define the second term of the right-hand side by taking the fluctuation of the potential into consideration. However, if such the potential is determined by calculation, the second term can be regarded as constant like the instance that the glass reference electrode is used.

As to the Equation (1) described above, while the element i is contacted with the standard solution, the output Voi of the element i is measured. According to the measured result, the sensitivity coefficients Si and Gi and the constant Ci are determined.

Next, in the pH sensor array, two elements i1 and i2 located near each other are selected.

While the sensor array is contacted with the sample, the output Voi1 of the first element i1 and the output Voi2 of the second element i2 are measured. The outputs of the two elements are as follows.

$$Voi1 = Si1 \times pHi1 + Gi1 \times Vrm + Ci1 \qquad \text{Equation (2)}$$

$$Voi2 = Si2 \times pHi2 + Gi2 \times Vrm + Ci2 \qquad \text{Equation (3)}$$

On the presumption that respective pHi1 and pHi2 of the sample contacted with the first element i1 and the second element i2 are equal each other, the potential Vrm of the sample is defined as follows.

$$Vrm = \{((Voi1-Ci1)/Si1) - ((Voi2-Ci2)/Si2)\}/(Gi1/Si1 - Gi2/Si2) \qquad \text{Equation (4)}$$

Accordingly, as to the first element i1 and the second element i2, the outputs Voi1 and Voi2, the sensitivity coefficients Si1, Si2, Gi1 and Gi2, and the constants Ci1 and Ci2 are substituted for the Equation (4) to determine the potential Vrm of the sample.

In this way, by referring to the determined potential Vrm, the output Voi of the element i, the sensitivity coefficients Si and Gi and the constant Ci, pHi of the sample contacted with the element i is defined as follows.

$$pHi = (Voi - Gi \times Vrm - Ci)/Si \qquad \text{Equation (5)}$$

Then, the pHi of the sample contacted with the element i and obtained above can be displayed on each site of the element i to display the pH distribution of the sample contacted with the sensor array.

According to the principle described above, the first aspect of the present invention is defined in the following.

A method for determining pH of a sample in contact with an element i constituting a pH sensor array by referring to output Voi of the element i defined as follows:

$$Voi = Si \times pHi + Gi \times Vrm + Ci \quad \text{Equation (1)}$$

wherein pHi is pH of the sample in contact with the element i, Vrm is potential of the sample, Si and Gi are sensitivity coefficients, and Ci is a constant, comprising:

a calibrating step of contacting the sensor array with a standard solution and calibrating the sensitivity coefficients Si and Gi and the constant Ci specific to the element i by referring to the output Voi of the element i;

a first measuring step of selecting a first element i1 and a second element i2 located near each other in the sensor array, contacting the sensor array with the sample, and measuring output Voi1 of the first element i1 and output Voi2 of the second element i2;

a potential determining step of determining potential Vrm of the sample, on the presumption that pHi1 and pHi2 of the sample contacted with the first element i1 and the second element i2 are equal each other, by referring to the output Voi1 of the first element i1 and the output Voi2 of the second element i2 measured in the first measuring step, and the sensitivity coefficients Si1, Si2, Gi1 and Gi2 and the constants Ci1 and Ci2 regarding the first element i1 and the second element i2 calibrated in the calibrating step;

a main measuring step of measuring output Voi of the element i by contacting the sensor array with the sample; and a pH determining step of determining pHi of the sample contacting the element i by referring to the potential Vrm determined in the potential determining step, the output Voi of the element i measured in the main measuring step, and the sensitivity coefficients Si and Gi and the constant Ci calibrated in the calibrating step.

According to the method for determining pH of the sample thus defined in the first aspect of the present invention, with each measurement of the sample, the potential Vrm of the sample is determined to calculate pH by referring to the determined potential Vrm. So, even if the potential of the sample fluctuates, pH can be determined exactly. In this way, except the glass reference electrode, a non-glass reference electrode including a Pt reference electrode, an Ag/AgCl reference electrode or the like can be adopted as a reference electrode contacted with a sample.

The characteristic required for the sample described above is conductive. So, the sample itself could be solution, sol, gel, or other solid substance for measuring pH.

A general-purpose standard solution indicating constant pH value can be used as a standard solution.

Although the structure of the element i of the pH sensor forming the pH sensor array is not particularly limited, the charge storage type pH sensor as disclosed in the patent document 1 is preferred for attaining the high density and the high sensitivity.

$$Voi = Si \times pHi + Gi \times Vrm + Ci \quad \text{Equation (1)}$$

For obtaining the sensitivity coefficients Si and Gi and the constant Ci of the Equation (1) above, it is explicitly required to solve the linear equation with three variables Voi, pHi and Vrm.

Therefore, for example, while the element i is contacted with the first standard solution indicating the first pH, the potential of the first standard solution is changed to measure the output Voi of the element i. Then, the sensitivity coefficient Gi is obtained from each potential and the output Voi of the element i which is obtained as to each potential.

Next, the second standard solution indicating the second pH different from the first pH is provided. The element i is contacted with the first standard solution and the second solution made equipotential each other to measure the output Voi of the element i as to the first solution and the second solution respectively. Then, the sensitivity coefficient Si is obtained from the sensitivity coefficient Gi determined above, the pH of each standard solution and the output Voi of the element i.

Next, the standard solution of known pH value, for example the first standard solution, is made a predetermined potential to obtain the output Voi. Then, the constant Ci is calculated from the output Voi and the sensitivity coefficients Si and Gi obtained above.

After the sensitivity coefficients Si and Gi and the constant Ci of the element i are determined, the plural elements, for example, the first element i1 and the second element i2, located near each other are selected so that the difference in the coefficients Si and Gi and the constants Ci of the selected elements is larger than a predetermined value. When the potential Vrm is determined in the potential determining step, if the difference in the coefficients Si and Gi and the constants Ci of the selected elements is small, the difference between the outputs of the selected elements also gets small likely to cause the error in the calculation of the potential Vrm.

The first element i1 and the second element i2 could be selected as the following.

The combinations of the pairs of the elements i located near each other in the sensor array are listed, as well as the differences in the coefficients Si and Gi and the constants Ci of the combinations. The weighting factor could be applied to each difference in the coefficients Si and Gi and the constants Ci to adopt the combination of the elements with the maximum addition of the differences.

Further, for excluding the defective elements, the combination of the elements with each of the differences in the coefficients Si and Gi and the constants Ci larger than another predetermined value could be eliminated.

The outputs Voi1 and Voi2 of the first element i1 and the second element i2 are as follows:

$$Voi1 = Si1 \times pHi1 + Gi1 \times Vrm + Ci1 \quad \text{Equation (2)}$$

$$Voi2 = Si2 \times pHi2 + Gi2 \times Vrm + Ci2 \quad \text{Equation (3)}$$

Here, even if the potential of the sample fluctuates, the potential of the sample indicates equipotential on all over the region of the sample at any given time. So, the second term of the right-hand side of the Equation indicates Vrm of the same value.

In addition, each pH of the sample contacted with the first element and the second element located near each other could indicate the different value. However, each pH of the sample is presumed to be equal from the viewpoint of the sensitivity of the pH sensor. So, in the Equation (1), pHi1=pHi2 is presumed.

In this way, at the time when the outputs Voi1 and Voi2 of the first element i1 and the second element i2 are obtained, the potential Vrm of the sample is as follows:

$$Vrm = \{((Voi1-Ci1)/Si1) - ((Voi2-Ci2)/Si2)\}/(Gi1/Si1 - Gi2/Si2) \quad \text{Equation (4)}$$

At the time when the outputs Voi1 and Voi2 of the first element i1 and the second element i2 are obtained, the output Voi of every element i among all of the elements is measured and stored.

As described above, since the potential Vrm of the sample at the time of measurement is determined, pHi of the sample contacted with each element i is obtained in the following Equation (5).

$$\text{pH}i=(Voi-Gi\times Vrm-Ci)/Si \qquad \text{Equation (5)}$$

In the Equation (5), the Voi is the measured value, the sensitivity coefficient Gi and Si and the constant Ci are the known values, and the Vrm is the determined value as described above.

Taking the fluctuation of the potential Vrm of the sample into consideration, it is preferred that the output of every element i is measured at the same time to execute the operation described above.

However, even if the reference electrode except the glass reference electrode is used, little variation of the potential of the sample is presumed for a short time. So, the potential determining step for determining the potential Vrm of the sample could be executed in advance to measure the output of every element i and calculate the pH of every element i thereafter.

The embodiment of the present invention is disclosed by referring to the determination of the hydrogen ion concentration index pH. In addition, if the output of the element i corresponds to the concentration of another ion, it is easily recognized for those skilled in the art to determine another ion concentration according to the same principle.

EMBODIMENTS (The First Embodiment)

Figure 1:
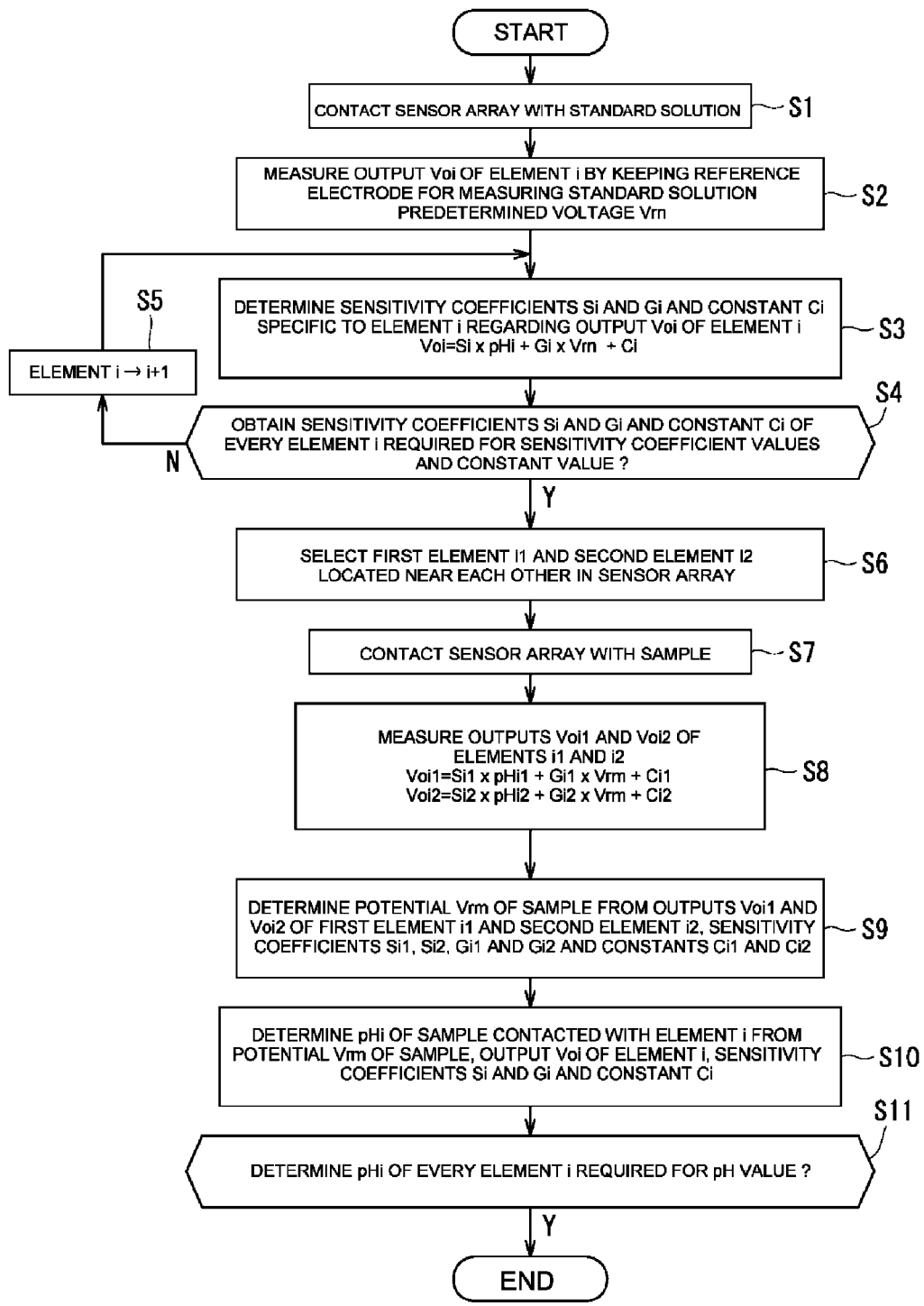
FIG. 1 is a flowchart showing a method of the first embodiment for determining pH of a sample.
Figure 2:
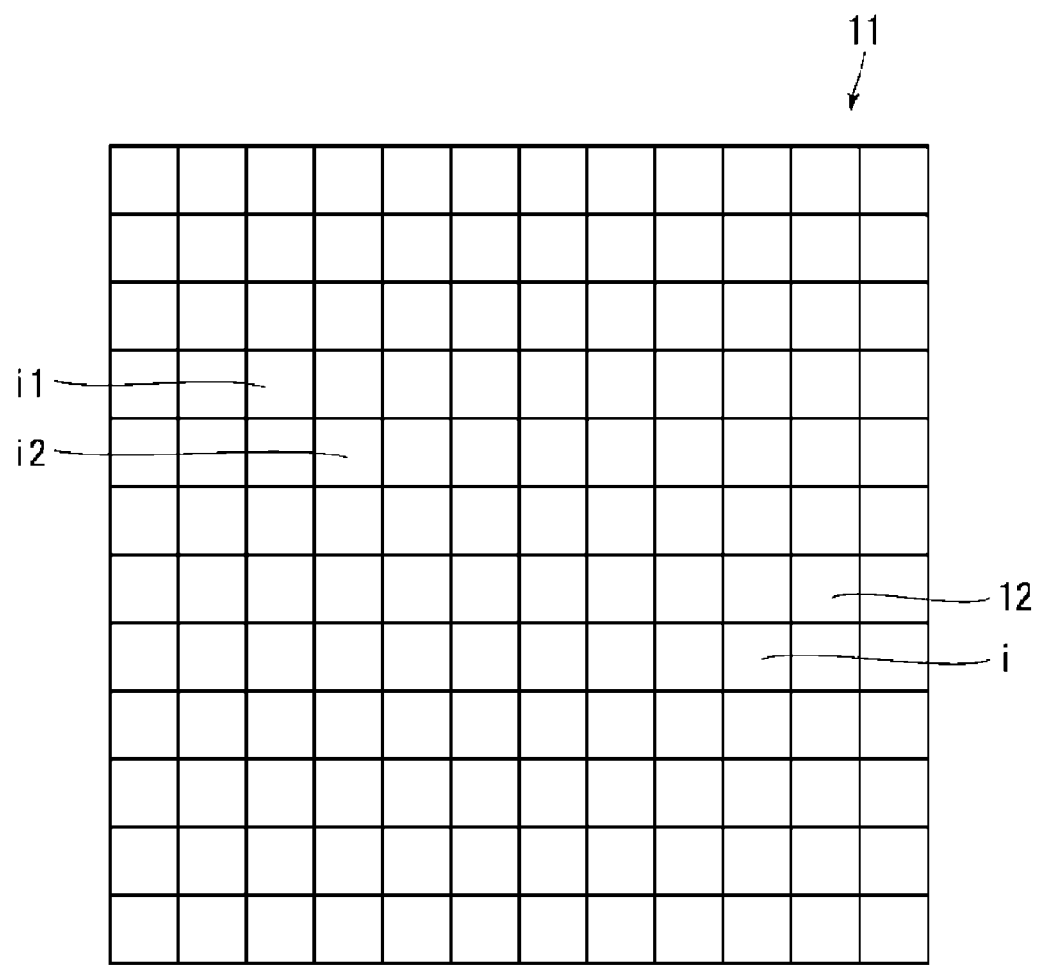
FIG. 2 is a conceptual diagram showing a sensor array of the first embodiment.

The first embodiment of the present invention is described in the following. FIG. 1 is a flowchart showing a method of the first embodiment of the present invention for determining pH. FIG. 2 is a conceptual diagram showing a sensor array of the first embodiment of the present invention.

Figure 3:
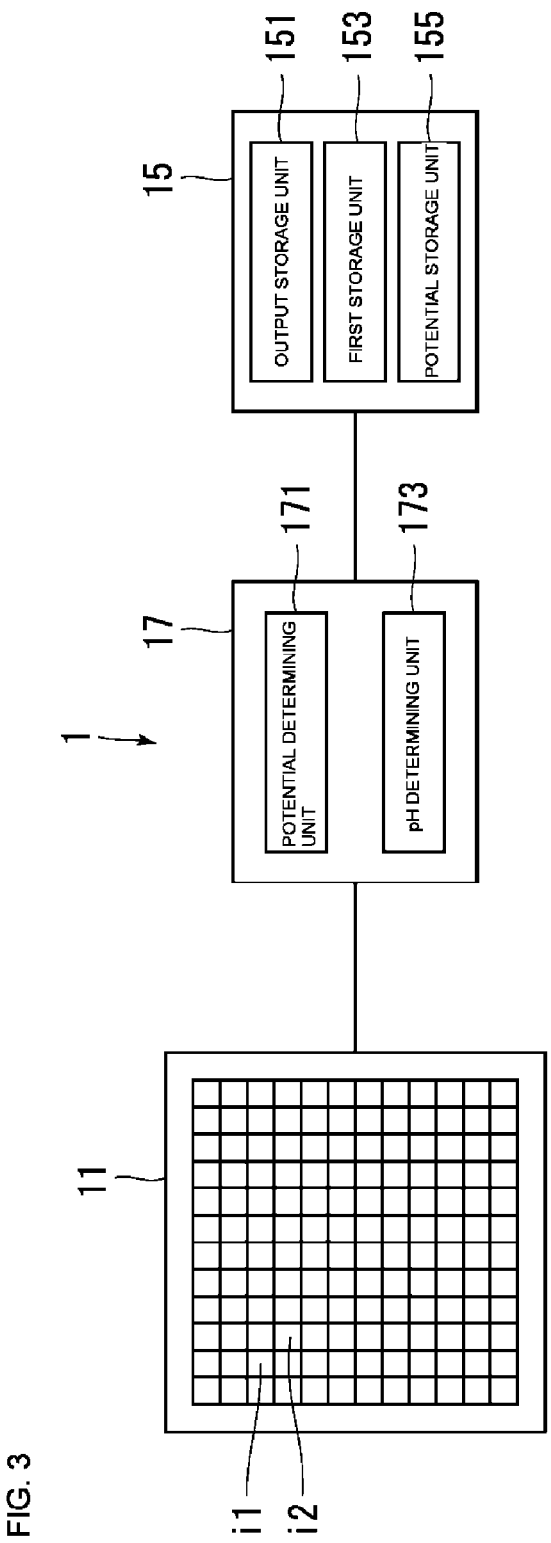
FIG. 3 is a block diagram showing the constitution of a device of the first embodiment of the present invention for determining pH.

As shown in FIG. 2, a sensor array 11 of the first embodiment of the present invention is made out of plural detecting pixels 12. Each of the detecting pixels 12 is provided with an element i. As shown in FIG. 3, the sensor array 11 is connected to a storage device 15 for storing a detected value and a controller 17 for controlling the sensor array 11 and the storage device 15 to determine pH of a sample.

By referring to the flowchart shown in FIG. 1, the method of the first embodiment of the present invention for determining pH is described in the following.

In the first place, the sensitivity coefficients Si and Gi and the constant Ci are determined, as referred to the steps 1-5 of the calibrating step.

The sensor array is contacted with a standard solution of known pH value, as referred to the step 1. In this stage, in addition to the sensor array, a reference electrode for measuring the standard solution is contacted with the standard solution to stabilize the potential of the standard solution. A glass electrode is preferred for the reference electrode for measuring the standard solution to define exactly the sensitivity coefficients Si and Gi and the constant Ci which determine the characteristic of each element i.

Next, the output Voi of the element i is measured by setting the reference electrode for measuring the standard solution at the predetermined potential Vrn, as referred to the step 2.

Then, as to the output Voi of the element i, namely $$Voi=Si\times \text{pH}i+Gi\times Vrn+Ci,$$

the sensitivity coefficients Si and Gi and the constant Ci pertinent to the element i are determined, as referred to the step 3.

The operation of the step 3 is executed all over the element i, as referred to the steps 4 and 5.

Next, the first measuring step is described in the following.

In the first place, on a basis of the sensitivity coefficients Si and Gi and the constant Ci specified in the calibrating step of the steps 1-5, two elements, namely the first element i1 and the second element i2 located near each other in the sensor array are selected as referred to the step 6.

As to the first element and the second element, large difference is preferable between the respective sensitivity coefficients Si and Gi and the respective constants Ci.

The first element i1 and the second element i2 selected are made to contact the sample so that the respective outputs Voi1 and Voi2 are measured as referred to the steps 7 and 8.

Here, the outputs Voi1 and Voi2 of the first element i1 and the second element i2 obtained in the step 8 and the respective sensitivity coefficients Si1, Si2, Gi1 and Gi2 and the respective constants Ci1 and Ci2 of the first element i1 and the second element i2 obtained in the step 4 are substituted for the Equation (1) to obtain Equations (2) and (3) in the following.

$$Voi1=Si1\times \text{pH}i1+Gi1\times Vrm+Ci1 \qquad \text{Equation (2)}$$

$$Voi2=Si2\times \text{pH}i2+Gi2\times Vrm+Ci2 \qquad \text{Equation (3)}$$

The pH values of the sample contacting the elements located near each other are presumed to be equal. So, on a presumption of pHi1=pHi2, the Equations (2) and (3) are transformed to a linear equation with two unknowns to obtain the potential Vrm of the sample, as referred to the step 9 of the potential determining step.

As described above, in the output equation of the element i, namely

Voi=Si×pHi+Gi×Vrm+Ci of Equation (1), all of the values except pHi are determined.

So, pHi is obtained in the following equation, as referred to the step S10 of the pH determining step.

$$\text{pH}i=(Voi-Gi\times Vrm-Ci)/Si$$

By making the sensor array contact the sample, measuring the output Voi of all of the elements i which constitute the sensor array, as referred to the main measuring step, and executing the operations of the step 10 on a basis of the outputs obtained, the pH of the sample contacting each element i is determined as referred to the step 11.

As shown in FIG. 3, the storage device 15 is provided with an output storage unit 151 for storing the output of the element i, the first storage unit 153 for storing the sensitivity coefficients Si and Gi and the constant Ci of the element i calibrated in the calibrating step, and the potential storage unit 155 for storing the potential of the sample which is determined. The output storage unit 151 includes the second storage unit for storing the outputs of the first element and the second element.

In addition, the controller 17 is provided with a potential determining unit 171 for determining the potential Vrm of the sample from the outputs Voi1 and Voi2 of the first element i1 and the second element i2 stored in the second storage unit and the sensitivity coefficients Si1, Si2, Gi1 and Gi2 and the constants Ci1 and Ci2 stored in the first storage unit 153, and the pH determining unit 173 for determining pHi of the sample in contact with the element i from the potential Vrm determined in the potential determining unit 171 and the sensitivity coefficients Si and Gi and the constant Ci stored in the first storage unit.

Figure 4:
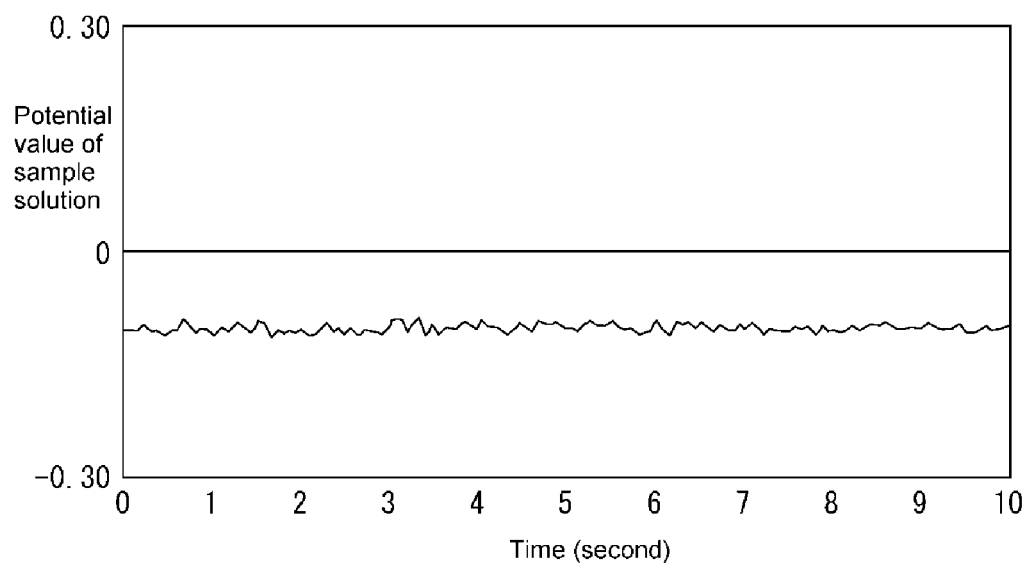
FIG. 4 is a diagram showing the time variation of the potential in the sample in contact with a non-glass electrode.

FIG. 4 shows the time variation of the potential of the sample solution. In the measurement of FIG. 4, an Ag/AgCl single body electrode was used as a reference electrode and pH 6.86 buffer solution was used as the sample solution. In addition, in the measurement of FIG. 4, a glass reference electrode with Ag/AgCl and saturated KCl was used as the standard.

Figure 5:
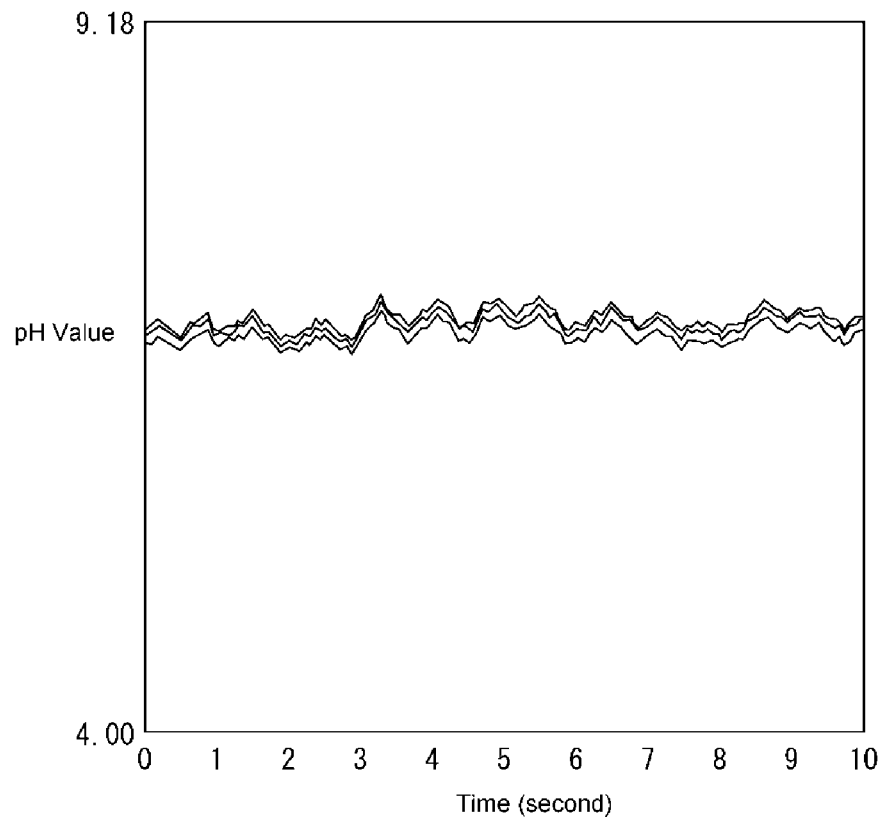
FIG. 5 is a diagram showing the time variation of pH obtained from the outputs of the elements when the method of the present invention for determining pH of the sample is executed.

FIG. 5 shows the time variation of the pH values calculated according to the method for determining pH described above, from the outputs of three arbitrarily selected elements which are obtained when the sensor array was contacted with the sample solution described above. By the way, two elements selected in the first measuring step are also chosen from such three arbitrarily selected elements.

Although the potential of the sample solution shifts and fluctuates, calculated pH values of all of the elements indicate about pH 6.86, as shown in the result of FIG. 5. So, we can understand the method of the present invention for determining pH is practical.

The present invention is not limited to the illustrated embodiments or examples alone, but may be changed and modified within the scope easily devised by those skilled in the art without departing from the spirit of the present invention.

DESCRIPTION OF THE REFERENCE NUMERALS

1 Device for determining pH
11 Sensor array
12 Pixel
15 Storage device
17 Controller

The invention claimed is:

1. A method for determining pH of a sample in contact with an element i constituting a pH sensor array by referring to output Voi of the element i defined as follows:

$$Voi = Si \times pHi + Gi \times Vrm + Ci \quad \text{Equation (1)}$$

wherein pHi is pH of the sample in contact with the element i, Vrm is potential of the sample, Si and Gi are sensitivity coefficients, and Ci is a constant,
comprising:
a calibrating step of contacting the pH sensor array with a standard solution and calibrating the sensitivity coefficients Si and Gi and the constant Ci specific to the element i by referring to the output Voi of the element i;

a first measuring step of selecting a first element i1 and a second element i2 located near each other in the pH sensor array, contacting the pH sensor array with the sample, and measuring output Voi1 of the first element i1 and output Voi2 of the second element i2;

a potential determining step of determining potential Vrm of the sample, on the presumption that pHi1 and pHi2 of the sample contacted with the first element i1 and the second element i2 are equal each other, by referring to the output Voi1 of the first element i1 and the output Voi2 of the second element i2 measured in the first measuring step, and a sensitivity coefficient Si1, Si2, Gi1 and Gi2 and a constant Ci1 and Ci2 calibrated for each of the first element i1 and the second element i2;

a main measuring step of measuring output Voi of the element i by contacting the pH sensor array with the sample; and a pH determining step of determining pHi of the sample contacting the element i by referring to the potential Vrm determined in the potential determining step, the output Voi of the element i measured in the main measuring step, and the sensitivity coefficients Si and Gi and the constant Ci calibrated in the calibrating step.

2. The method according to claim 1,
wherein the calibrating step includes:
a first step of contacting the element i with a first standard solution indicating first pH, measuring output Voi of the element i by changing potential of the first standard solution, and obtaining the sensitivity coefficient Gi by referring to the potential and the output Voi of the element i; and
a second step of preparing a second standard solution indicating second pH different from the first pH, contacting the element i with the first standard solution and the second standard solution arranged with equal potential each other, measuring output Voi of the element i in each of the first standard solution and the second standard solution, and obtaining the sensitivity coefficient Si by referring to pH in each of the first standard solution and the second standard solution and the output Voi of the element i.

3. The method according to claim 2,
the first element i1 and the second element i2 selected in the first measuring step have differences in respective sensitivity coefficients Si and Gi, as well as the constant Ci thereof, and the differences are larger than or equal to predetermined value.

4. The method according to claim 2,
wherein in the potential determining step, potential Vrm of the sample is obtained by using a following equation:

$$Vrm = \{((Voi1-Ci1)/Si1) - ((Voi2-Ci2)/Si2)\}/(Gi1/Si1 - Gi2/Si2).$$

5. The method according to claim 4,
wherein in the pH determining step, pHi of each element i is obtained by using a following equation:

$$pHi = (Voi - Gi \times Vrm - Ci)/Si.$$

6. The method according to claim 1, including contacting a non-glass reference electrode including a Pt reference electrode or an Ag/AgCl reference electrode with the sample as a reference electrode in the first measuring step and the main measuring step.

7. A method for determining ion concentration of a sample in contact with an element i constituting an ion concentration sensor array by referring to output Voi of the element i defined as follows:

$$Voi = Si \times Qi + Gi \times Vrm + Ci \quad \text{Equation (1')}$$

wherein Qi is ion concentration of the sample in contact with the element i, Vrm is potential of the sample, Si and Gi are sensitivity coefficients, and Ci is a constant, comprising:

a calibrating step of contacting the ion concentration sensor array with a standard solution and calibrating the sensitivity coefficients Si and Gi and the constant Ci specific to the element i by referring to the output Voi of the element i;

a first measuring step of selecting a first element i1 and a second element i2 located near each other in the ion concentration sensor array, contacting the ion concentration sensor array with the sample, and measuring output Voi1 of the first element i1 and output Voi2 of the second element i2;

a potential determining step of determining potential Vrm of the sample, on the presumption that respective ion concentrations Qi1 and Qi2 of the sample contacted with the first element i1 and the second element i2 are equal each other, by referring to the output Voi1 of the first element i1 and the output Voi2 of the second element i2 measured in the first measuring step, and a sensitivity coefficient Si1, Si2, Gi1 and Gi2 and a constant Ci1 and Ci2 calibrated for each of the first element i1 and the second element i2;

a main measuring step of measuring output Voi of the element i by contacting the ion concentration sensor array with the sample; and an ion concentration determining step of determining ion concentration Qi of the sample contacting the element i by referring to the potential Vrm determined in the potential determining step, the output Voi of the element i measured in the main measuring step, and the sensitivity coefficients Si and Gi and the constant Ci calibrated in the calibrating step.

8. A device for determining pH of a sample in contact with an element i constituting a pH sensor array by referring to output Voi of the element i defined as follows:

$$Voi = Si \times pHi + Gi \times Vrm + Ci \qquad \text{Equation (1)}$$

wherein pHi is pH of the sample in contact with the element i, Vrm is potential of the sample, Si and Gi are sensitivity coefficients, and Ci is a constant, comprising:

a first storage unit for storing the sensitivity coefficients Si and Gi and the constant Ci specific to the element i and calibrated by referring to the output Voi of the element i measured with the pH sensor array contacted with a standard solution;

a second storage unit for storing output Voi1 and output Voi2 of a first element i1 and a second element i2 measured with the pH sensor array contacted with the sample, the first element i1 and the second element i2 being located near each other;

a potential determining unit for determining potential Vrm of the sample, on the presumption that pHi1 and pHi2 of the sample contacted with the first element i1 and the second element i2 are equal each other, by referring to the output Voi1 of the first element i1 and the output Voi2 of the second element i2 stored in the second storage unit, and a sensitivity coefficient Si1, Si2, Gi1 and Gi2 and a constants Ci1 and Ci2 calibrated for each of the first element i1 and the second element i2 and stored in the first storage unit; and a pH determining unit for determining pHi of the sample in contact with the element i by referring to the potential Vrm determined by the potential determining unit, and the sensitivity coefficients Si and Gi and the constant Ci stored in the first storage unit.

* * * * *